United States Patent
Moritz et al.

(10) Patent No.: US 6,450,940 B1
(45) Date of Patent: Sep. 17, 2002

(54) MAGNETIC STIMULATION DEVICE

(75) Inventors: Michael Moritz, Mistelgau; Franz Schmitt, Erlangen; Peter Schweighofer, Nürnberg; Peter Havel, Biburg, all of (DE)

(73) Assignee: Peter Martin Havel, Munich (DE)

( * ) Notice: Subject to any disclaimer, the term of this patent is extended or adjusted under 35 U.S.C. 154(b) by 0 days.

(21) Appl. No.: 09/446,878

(22) PCT Filed: May 11, 1999

(86) PCT No.: PCT/DE99/01426
§ 371 (c)(1),
(2), (4) Date: Sep. 8, 2000

(87) PCT Pub. No.: WO99/59674
PCT Pub. Date: Nov. 25, 1999

(30) Foreign Application Priority Data

May 15, 1998 (DE) ............................ 198 22 018

(51) Int. Cl.[7] ................................ A61N 1/00
(52) U.S. Cl. ........................................ 600/13
(58) Field of Search ................ 600/13, 14, 15, 600/372; 607/2; 128/897, 898

(56) References Cited

U.S. PATENT DOCUMENTS

| | | | | |
|---|---|---|---|---|
| 4,850,959 A | * | 7/1989 | Findl | 600/14 |
| 4,940,453 A | | 7/1990 | Cadwell | |
| 5,061,234 A | | 10/1991 | Chaney | |
| 5,167,229 A | * | 12/1992 | Peckman et al. | 600/13 |
| 5,224,922 A | * | 7/1993 | Kurtz | 600/13 |
| 5,743,844 A | | 4/1998 | Tepper et al. | |
| 5,782,874 A | * | 7/1998 | Loos | 607/2 |
| 5,991,649 A | * | 11/1999 | Garfield et al. | 600/372 |

FOREIGN PATENT DOCUMENTS

| | | |
|---|---|---|
| DE | OS 36 07 235 | 9/1987 |
| DE | OS 41 32 428 | 4/1993 |
| DE | OS 196 07 704 | 9/1996 |
| EP | 0 182 160 | 5/1986 |
| GB | 2 298 370 | 9/1996 |

OTHER PUBLICATIONS

"Neuro–und Sinnes physiologic," Schmidt, Chapters 2 & 3 (1995).

"Entwicklung, Optimierung und Erprobung neuer Geräte für die magnetomotorische Stimulation von Nervenfasern," Schmid et al., Biomedizinische Technik, vol. 38 (1993) pp. 317–324.

* cited by examiner

*Primary Examiner*—Kevin Shaver
*Assistant Examiner*—Brian Szmal
(74) *Attorney, Agent, or Firm*—Schiff Hardin & Waite

(57) ABSTRACT

A magnetic stimulation apparatus for triggering action potentials, particularly in more deeply disposed, neuromuscular tissue of a patient as well, has at least one stimulation coil that has terminals connected to the output of a current-generating unit offers greater degrees of freedom in the selection of the current pulse shapes because the current-generating unit provides current pulses generated in non-resonant fashion for the stimulation coil.

13 Claims, 3 Drawing Sheets

MAGNETIC STIMULATION DEVICE

BACKGROUND OF THE INVENTION

1. Field of the Invention

The present invention is directed to a magnetic stimulation apparatus of the type having at least one stimulation coil that has terminals connected to the output of a current-generating unit.

2. Description of the Prior Art

Magnetic stimulation apparatuses serve for magnetic stimulation of nerve fibers and muscle tissue in the field of medical diagnostics and therapy. Compared to electrical stimulation with stimulation current, the advantage of magnetic pulse stimulation lies in the lower pain of the stimulation, since no higher current densities in the region of the pain receptors of the skin occur given magnetic pulse stimulation. A further advantage of magnetic stimulation lies in the higher penetration capability, as a result whereof the excitation of tissue lying deeper is also possible, particularly nerve fibers that lie deeper.

The book by R. F. Schmidt (editor), "Neuro-und Sinnesphysiologie", Springer, second, amended edition 1995, Chapters 2 and 3, contains an exact description of neuro-physiological occurrences. The nerve system, for example, coordinates the activities of the various organs and reactions of the body to the environment. This mainly occurs due to modifications of the potential of nerve cells. All cells have a quiescent potential. At the quiescent potential, all membrane currents of a cell are in equilibrium. When the membrane potential is depolarized by an additional membrane current that, for example, proceeds into the cell due to an external influence, then this is accompanied by a change in potential, referred to as an action potential. The aforementioned, depolarizing membrane current is also called stimulus. The trigger potential for an action potential is called threshold. The equilibrium of the membrane currents changes at threshold. Additional membrane currents that depolarize the membrane occur for a short time. This condition is also called excitation. An action accompanies an action potential. Thus, for example, each spasm of a muscle fiber is accompanied by an action potential in the muscle fiber, and each reaction of a sensory cell to a sensory stimulation is accompanied by action potentials.

European Application 0 182 160 discloses an apparatus for generating electromagnetic pulses with a semicircular shape and a frequency of 100 Hz that, in particular, serves for promoting the micro-circulation of the blood in the region of the hair roots and the skin, for example to prevent hair loss. To that end, a diode rectifier bridge in Graetz circuitry that feeds a pulse-generating coil is connected to an A.C. voltage transformer.

German OS 36 07 235 discloses an apparatus for generating unipolar air ions and electromagnetic pulse fields for reducing the human reaction time while simultaneously increasing the attention readiness. For generating the electromagnetic pulse fields, a frequency generator that generates a frequency in the range from 8 Hz through 10 Hz and having a following out-coupling amplifier and a coil generating the pulse field is connected to a voltage source.

German OS 41 32 428 discloses a magneto-therapy apparatus for magneto-therapeutic treatment. For generating a pulse setting magnetic field with a pulse repetition rate between 0.25 Hz and 2 Hz, an unstable multi-vibrator is connected to a battery, this multi-vibrator feeding two cylindrical coils filled with iron. The apparatus is fashioned as a pocket apparatus.

U.S. Pat. No. 5,743,844 discloses an apparatus for therapy with pulsating electromagnetic fields for promoting healing of bone and body tissue, particularly in an embodiment as a battery-powered apparatus that can be worn on the body. To that end, a coil generating the magnetic field is supplied from two voltage sources of different voltage height via a specific circuit that contains two field effect transistors and two capacitors as critical elements. The aforementioned circuit thereby has a fixed pulse-to-pause time relationship.

The devices disclosed in the above-cited documents are all designed such that the magnetic pulsed or, alternating fields they generate act on the human body below the threshold for triggering action potentials. The effects in the human body that can thus actually be achieved are partly very diffuse and scientifically controversial. Magnetic stimulation devices that intentionally trigger action potentials, particularly in more deeply disposed neural-muscular tissue, however, constitute an entirely different category of devices. Not only are the use and therapeutic effect of these devices different but they operate at multiply higher electrical powers to be provided, this being reflected in correspondingly high current and voltage values. The devices disclosed in the above-cited documents are not suitable for this purpose due to their overall low-voltage and micro-current-oriented design.

A magnetic stimulation apparatus for triggering action potentials, in more deeply disposed, neuro-muscular tissue as well, is described in the article by M. Schmid, T. Weyh and B. -U. Meyer, "Entwicklung, Optimiereung und Erprobung neuer Geräte für die magnetomotorische Stimulation von Nervenfasern", Biomedizinische Technik, 38 (1993), pages 317 through 324. It comprises a stimulation coil to which current pulses generated in resonant fashion are supplied. The current-generating circuitry required for generating the current pulses comprises a controllable power pack part as well as a high-voltage capacitor that forms a parallel resonant circuit together with the stimulation coil, i.e. it operates as a resonant circuit. The high-voltage capacitor is charged by the controllable power pack part and thereby accumulates the pulse energy required for the output of a current pulse.

The resonant frequency of the parallel resonant circuit formed by the stimulation coil and the high-voltage capacitor is defined by the selection of the capacitance of the high-voltage capacitor and by the inductivity of the stimulation coil and lies in the range from 1 through 3 kHz. When the capacitance of the high voltage capacitor is varied, then the resonant frequency of the parallel resonant circuit and, thus, the rate of the current rise in the stimulation coil can be modified. The stimulus intensity is defined by the initial voltage at the high-voltage capacitor. Only the repetition rate, which lies in the area around 10 Hz, can be set as a further parameter.

Further, German OS 196 07 704 A1 discloses an apparatus for magnetic excitation of neural-muscular tissue. The known apparatus comprises an excitation coil (stimulation coil) that forms a parallel resonant circuit together with a storage capacitor (high-voltage capacitor), i.e. likewise works as 5 resonant circuit. Given this apparatus as well, resonant frequencies can only be realized in the range from 1 through 3 kHz.

SUMMARY OF THE INVENTION

An object of the present invention is therefore to create a magnetic stimulation apparatus for triggering action potentials in more deeply disposed neural-muscular tissue as well that offers greater degrees of freedom in the selection of the current pulse shapes.

The above object is achieved in an inventive magnetic stimulation apparatus having at least one stimulation coil that has terminals connected to the output of at least one current-generating unit, whereby the current-generating unit offers non-resonantly generated current pulses for the stimulation coil.

By abandoning resonant operation, greater degrees of freedom can be achieved in the selection of the current pulse shapes. Moreover, no regulatable power pack parts having specific charging circuits are required.

Since the stimulation coil—by contrast to the comparable magnetic stimulation devices of the prior art—is not part of a parallel resonant circuit, further degrees of freedom derive due to the selection of the inductivity of the stimulation coil.

In an embodiment the current-generating unit includes at least one controllable power converter having at least one power semiconductor switch with short switching times that can be switched on and off.

As used herein the term "short switching time" means switching times of approximately 1 µs or less.

The power semiconductor switches that can be switched on and off and that are provided in the aforementioned embodiment must exhibit short switching times, so that transistors, particularly IGBTs or MOSFETs, are preferably currently employed therefor.

DESCRIPTION OF THE PREFERRED EMBODIMENTS

Figure 1:
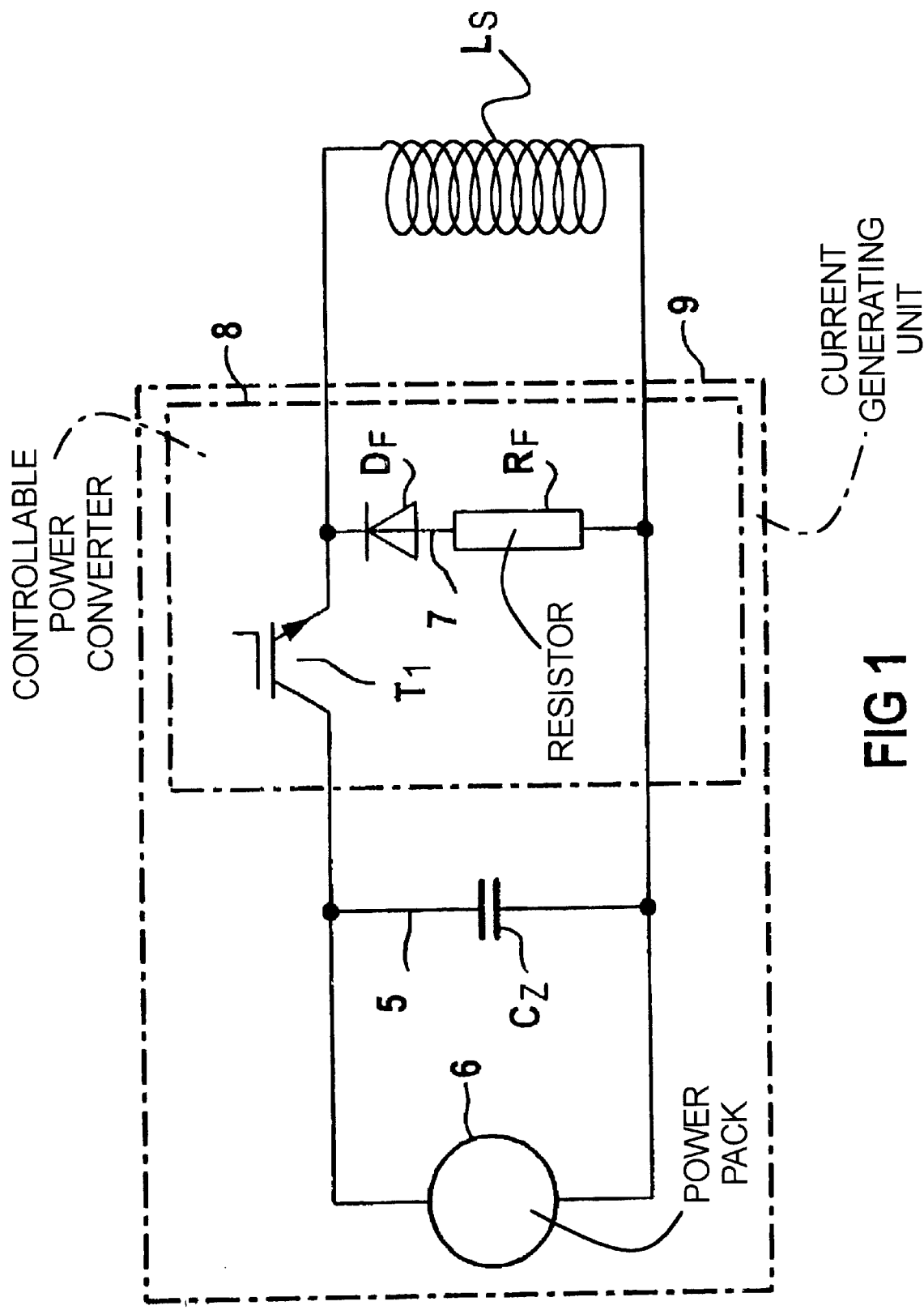
FIG. 1 is a circuit diagram of a magnetic stimulation apparatus constructed and operating in accordance with the principles of the present invention.

FIG. 1 shows an embodiment of an inventive magnetic stimulation apparatus. The apparatus includes at least one stimulation coil $L_s$ that has terminals connected to the output of a current-generating unit 9. The current-generating unit 9 is formed, for example, by the parallel circuit of a power pack 6, which need not be controllable and is preferably implemented as high-voltage power pack part, an intermediate voltage circuit 5 and a controllable power converter 8 that contains at least one power semiconductor switch $T_1$ with short switching times that can be switched on and off. The intermediate voltage circuit includes at least one intermediate circuit capacitor $C_z$ and is charged by the power pack part.

Given the magnetic stimulation apparatus shown in FIG. 1, the stimulation coil is supplied with the energy stored in the intermediate circuit capacitor after the power semiconductor switch is turned on and a current pulse is thus triggered. After the power semiconductor switch is turned off, the current flowing in the stimulation coil is dismantled via an unbiased branch 7 arranged in the controllable power converter. At least one unbiased diode $D_F$ is arranged in the unbiased branch. In the illustrated exemplary embodiment, a resistor $R_F$ is connected in series with the unbiased diode $D_F$ in the unbiased branch. The unbiased resistor can also be omitted if the parasitic resistances in the circuit are adequately high.

Figure 2:
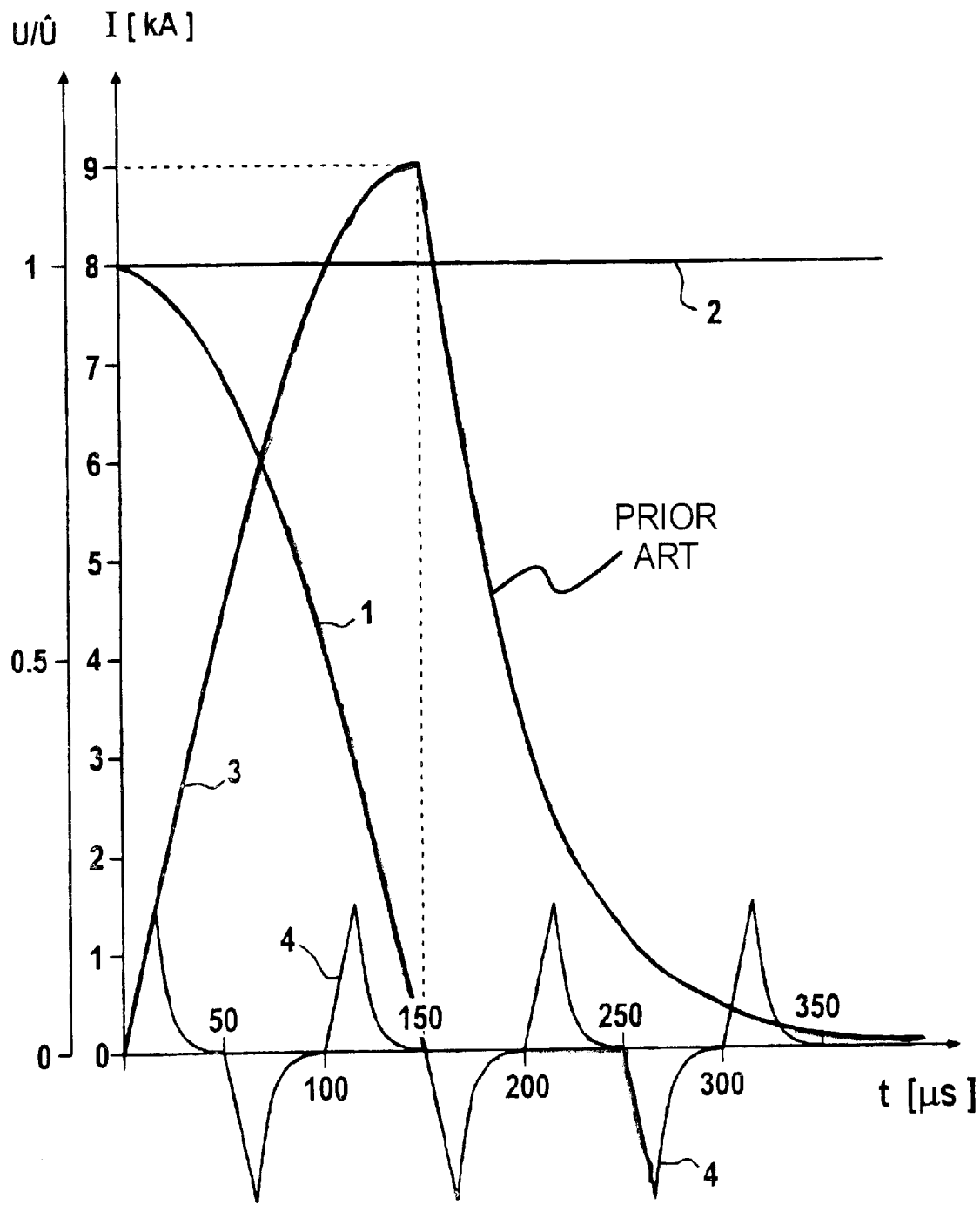
FIG. 2 shows a curve of current pulses that are generated in non-resonant fashion in an embodiment of the inventive magnetic stimulation apparatus, a voltage curve corresponding thereto which is produced within the current-generating unit of the inventive apparatus, and current and voltage curves that are generated by an apparatus according to the prior art.

In FIG. 2, curve 1 is the curve of the output voltage of a high-voltage capacitor given a current-generating unit in a magnetic stimulation apparatus according to the prior art. The high-voltage capacitor, which forms a parallel resonant circuit with the stimulation coil, is charged by a controllable power pack and thereby accumulates energy required for the output of a current pulse.

Curve 2 is the curve from an output voltage of an intermediate circuit capacitor in an intermediate voltage circuit of an inventive magnetic stimulation apparatus. The intermediate circuit capacitor $C_z$ is charged by the power pack 6, which need not be controllable, and supplies voltage to the controllable power converter 8 when it discharges.

The output voltage curve 1 as well as the output voltage curve 2 are shown referenced to the peak value $U/\hat{U}$ of the voltage. The maximum values of the output voltage curves 1 and 2 are thus equal to one.

Given the magnetic stimulation apparatus according to the prior art, the discharge of the high-voltage capacitor leads, according to the voltage curve 1, to a current pulse (reference 3) through the stimulation coil.

The current pulse represented by curve 3 rises during the discharge of the high-voltage capacitor in such a prior art stimulator, lasting 150 µs, up to an amplitude value of 9 kA (voltage curve 1). When the amplitude value of 9 kA is reached, the voltage has dropped to zero. Since energy is no longer resupplied by the high-voltage capacitor, the current pulse decays within a decay time of approximately 150–200 µs. After a renewed charging of the high-voltage capacitor in such a prior art stimulator, the above-described, resonant generation of a current pulse begins anew. The current pulse 3 generated in resonant fashion and shown in FIG. 2 thus has a pulse width of 150 µs plus decay time.

Compared thereto, the output voltage 2 across the intermediate circuit capacitor $C_z$ given the inventive magnetic stimulation apparatus remains constant, since the current pulses shown as curve 4 in FIG. 2 are produced in a non-resonant fashion according to the invention. Given the inventive pulsing, alternating current pulses 4 are generated in very rapid succession. The current pulses of curve 4 shown in FIG. 2 exhibit, for example, a current amplitude of 1.5 kA and a pulse width or pulse duration of 12.5 µs plus decay time. Including the decay time, the pulse duration thus amounts to 50 µs (rise time 12.5 µs, decay time 37.5 µs). However, current amplitudes up to 3 kA are possible within the scope of the invention. Moreover, rise times (pulse widths without decay times) of less then 50 µs can be realized for the current pulses generated in non-resonant fashion.

In the curve 4 shown in FIG. 2, the steepness of the first current pulse of the curve 4 generated in non-resonant fashion corresponds to the respective initial steepness of the current curve 3 generated in resonant fashion (current pulse according to the prior art). However, the first current pulse of curve 4 generated in non-resonant fashion is terminated quickly (after approximately 12.5 µs) and a further current of the curve 4 generated in non-resonant fashion is started soon thereafter (approximately 37.5 µs after the termination of the preceding current pulse).

In the illustrated exemplary embodiment, all current pulses of the curve 4 have the same pulse width. However, it is just as easily possible within the scope of the invention to generate different pulse widths and, resulting therefrom, different current amplitudes in a non-resonant fashion.

By terminating each current pulse 4 of the curve relatively quickly and starting further current pulse soon thereafter, the required maximum current maximum current drops considerably. In the illustrated exemplary embodiment, the required maximum current drops from 9 kA to 1.5 kA, whereby maximum currents up to approximately 3 kA are possible within the scope of the invention. The high operating frequencies required for this purpose can be realized unproblemmatically by IGBT and MOSFET modules.

Due to the fact that the current pulses are generated in non-resonant fashion given the magnetic stimulation apparatus of the invention, the output voltage $U_{CZ}$ (voltage curve 2) across the intermediate circuit capacitor $C_Z$ remains constant.

Figure 3:
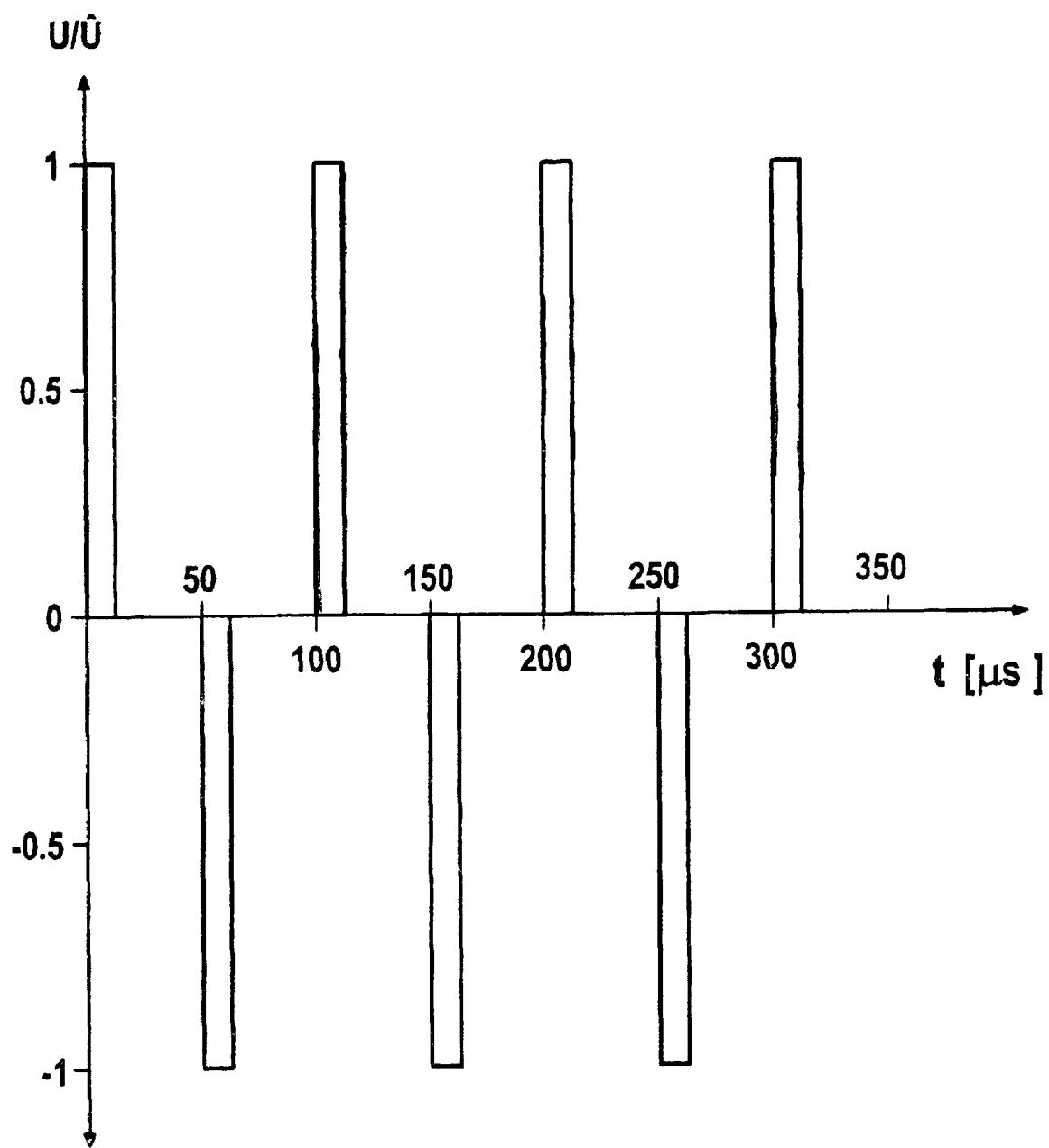
FIG. 3 shows a curve of the voltage at the stimulation coil that corresponds to the curve of the current pulses of FIG. 2 generated by the inventive stimulation apparatus.

The non-resonant current pulses of the curve 4 shown in FIG. 2 lead to the curve of the voltage across the stimulation coil $L_S$ that is shown in FIG. 3. The current pulse widths of 12.5 $\mu$s lead to square-wave voltage pulses that likewise exhibit a pulse width 12.5 $\mu$s and that correspond in polarity to the current pulses of the curve 4 generated in non-resonant fashion. The voltage across the stimulation coil $L_S$ is again referenced to its peak value $U/\hat{U}$ in FIG. 3.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic stimulation apparatus for non-invasively triggering action potentials, particularly in more deeply disposed, neuro-muscular tissue of a patient, comprising a current generating unit and at least one stimulation coil having terminals connected to an output of the current-generating unit, the current-generating unit supplying current pulses generated in non-resonant fashion to the stimulation coil which cause said stimulation coil to generate a magnetic field that directly depolarizes nerve cells to produce said action potential.

2. A magnetic stimulation apparatus according to claim 1, wherein the current-generating unit comprises at least one controllable power converter having at least one power semiconductor switch with short switching times that can be switched on and off.

3. A magnetic stimulation apparatus according to claim 1, wherein said current generator generates said current pulses with an amplitude in a range from 1.5 kA through 3 kA.

4. A magnetic stimulation apparatus according to claim 3, wherein said current generator generates said current pulses with a maximum rise time of 50 $\mu$s.

5. A magnetic stimulation apparatus according to claim 1, wherein said current generator generates said current pulses with a constant amplitude.

6. A magnetic stimulation apparatus according to claim 1, wherein said current generator generates said current pulses with a constant duration.

7. A magnetic stimulation apparatus according to claim 1, wherein said current generator generates said current pulses with a constant amplitude and duration.

8. A method for non-invasively triggering action potentials in neuro-muscular tissue of a patient, comprising the steps of:

non-invasively placing a stimulation coil in relation to a muscle; and supplying a current to said coil and thereby causing said coil to generate a magnetic field which directly depolarizes nerve cells in said muscle to trigger action potentials in said muscle.

9. A method as claimed in claim 8 wherein the step of supplying a current to said stimulation coil comprises supplying current pulses to said stimulation coil having an amplitude in a range from 1.5 kA through 3 kA.

10. A method as claimed in claim 9 comprising supplying said current pulses with a maximum rise time of 50 $\mu$s.

11. A method as claimed in claim 9 comprising supplying said current pulses with a constant amplitude.

12. A method as claimed in claim 9 comprising supplying said current pulses with a constant duration.

13. A method as claimed in claim 9 comprising supplying said current pulses with a constant amplitude and duration.

* * * * *